US00PP17933P3

(12) United States Plant Patent
Jandrew

(10) Patent No.: US PP17,933 P3
(45) Date of Patent: Aug. 21, 2007

(54) ***PENSTEMON* PLANT NAMED 'PHENI VIO'**

(50) Latin Name: *Penstemon hartwegii*
Varietal Denomination: Pheni Vio

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 1 day.

(21) Appl. No.: 11/301,490

(22) Filed: Dec. 13, 2005

(65) Prior Publication Data

US 2007/0136912 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new *Penstemon* plant particularly distinguished by medium sized, deep violet flowers with white throats, long, many-flowered inflorescences, early flowering, medium-green foliage with relatively narrow lanceolate leaves, fairly vigorous growth, and an upright plant habit with medium to long steady stems and very good branching ability is disclosed.

2 Drawing Sheets

Genus and species: *Penstemon hartwegii* Benth.
Variety denomination: 'Pheni Vio'.

BACKGROUND OF THE NEW PLANT

The present invention comprises a new and distinct cultivar of *Penstemon,* botanically known as *Penstemon hartwegii,* and hereinafter referred to by the cultivar name 'Pheni Vio'. The new cultivar originated from a hybridization made in 2002 in Gilroy, Calif. The female parent is a proprietary white-flowered *Penstemon* plant designated '103-3' (unpatented), and the male parent is a proprietary *Penstemon* plant designated '114-1' (unpatented) having violet flowers. The seeds produced by the hybridization were sown in November 2002, and the resulting seedlings were selected in May 2003. A single plant selection was chosen for further evaluation and for asexual propagation in the summer of 2003.

The new cultivar was created in 2002 in Gilroy, Calif. and has been asexually reproduced repeatedly by vegetative cuttings and tissue culture in Gilroy, Calif. over a three-year period. The plant has also been trialed at Gilroy, Calif., and Hillscheid, Germany. The present invention has been found to retain its distinctive characteristics through successive asexual propagations.

Plant Breeder's Rights for this cultivar were applied for in Europe on Oct. 14, 2005 and in Canada on Mar. 29, 2005.

SUMMARY OF THE INVENTION

The following are the most outstanding and distinguishing characteristics of this new cultivar when grown under normal horticultural practices in Gilroy, Calif. and Hillscheid, Germany.

1. Medium sized, deep violet flowers with white throats;
2. Long, many-flowered inflorescences;
3. Early flowering;

4. Medium green foliage with relatively narrow lanceolate leaves;
5. Fairly vigorous growth;
6. An upright plant habit with medium to long steady stems; and
7. Very good branching ability.

DESCRIPTION OF PHOTOGRAPHS

This new *Penstemon* plant is illustrated by the accompanying photographs which show blooms, buds, and foliage of the plant in full color; the colors shown are as true as can be reasonably obtained by conventional photographic procedures. The photographs are of whole plants about 3 months old, grown in a field in Gilroy, Calif. in mid July 2005.

DESCRIPTION OF THE NEW CULTIVAR

Figure 1:
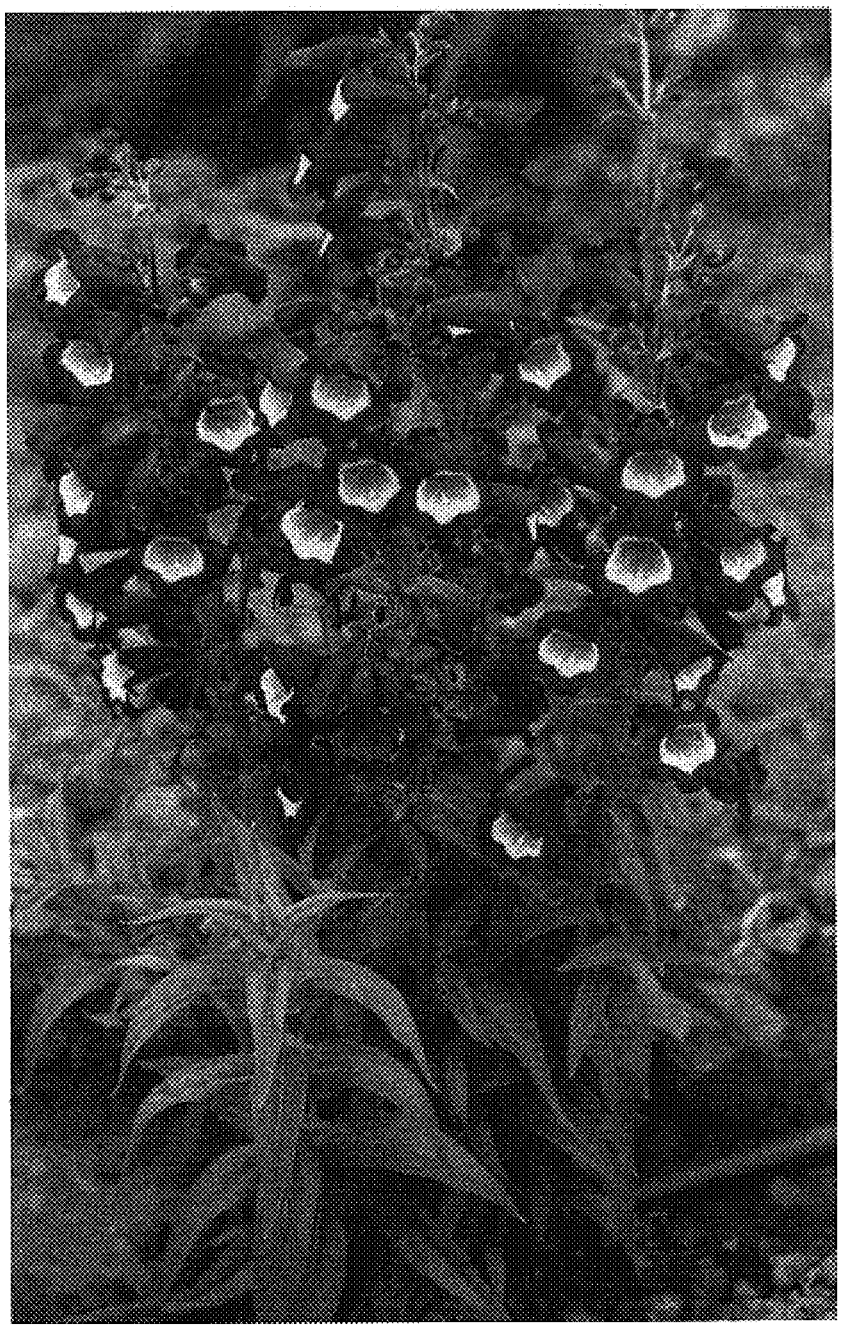
FIG. 1 shows the overall plant habit, including blooms, buds, mature foliage, and plant habit.
Figure 2:
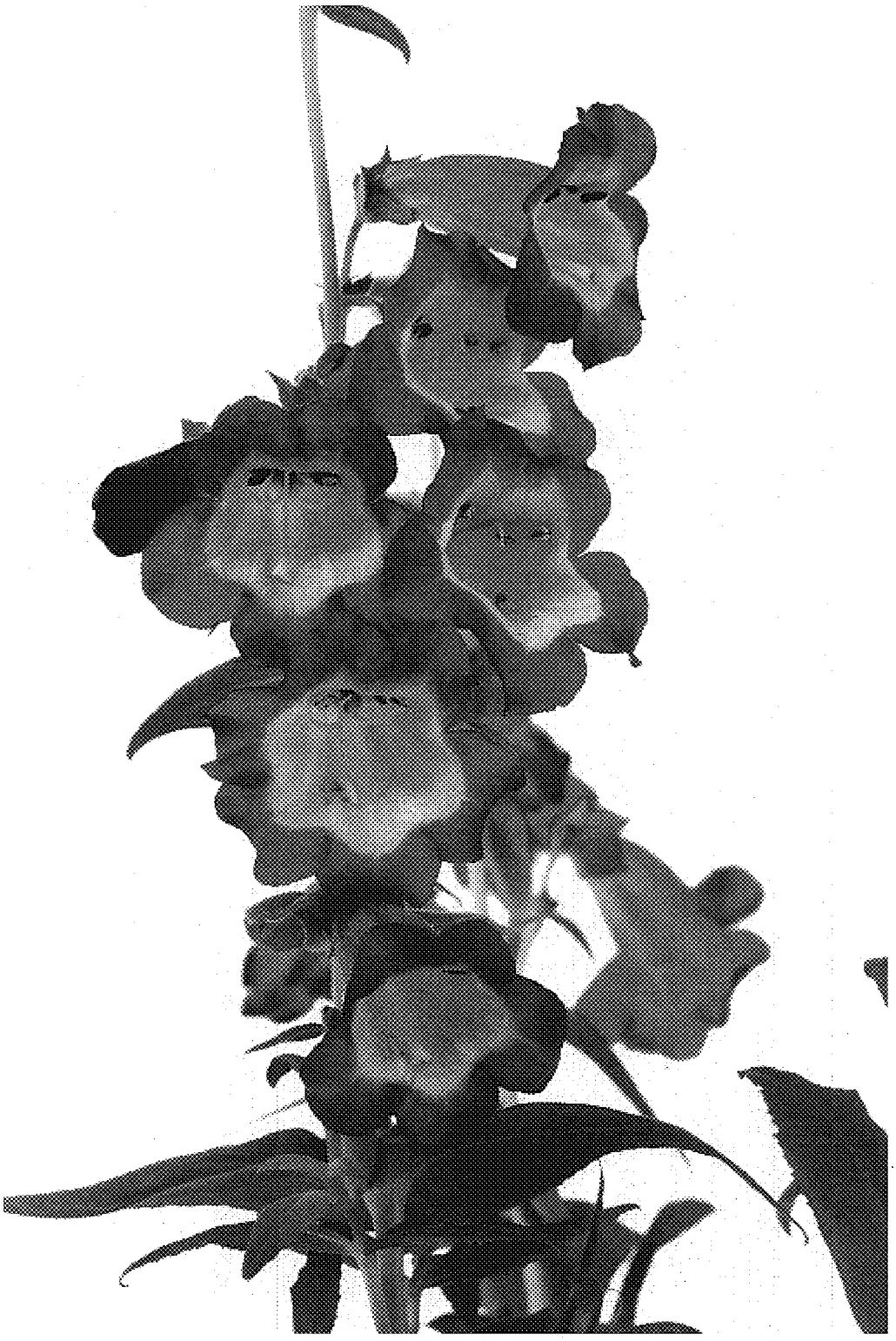
FIG. 2 shows a close-up of the mature inflorescences.

The following detailed descriptions set forth the distinctive characteristics of 'Pheni Vio'. The data which define these characteristics were collected from asexual reproductions carried out in Gilroy, Calif. The plant history was taken on nine-to eleven-week-old plants grown in Hillscheid, Germany in 2005. Rooted cuttings were planted into 12-cm plastic pots placed in a greenhouse. The plants were not pinched, so they mostly developed into single-stem plant habits. Most observations were made after nine weeks at the beginning of flowering. Color readings were taken under natural light. Color references are primarily to the R.H.S. Colour Chart of The Royal Horticultural Society of London (R.H.S.) (2001 edition).

DETAILED BOTANICAL DESCRIPTION OF THE NEW PLANT

Classification:

*Family.*—Scrophulariaceae.

*Botanical name.*—*Penstemon hartwegii* Benth.

Parentage:

*Female parent.*—'103-3' a proprietary white-flowered *Penstemon* plant (unpatented).

*Male parent.*—'114-1' a proprietary violet-flowered *Penstemon* plant (unpatented).

Growth:

*Form.*—Herbaceous perennial; suffrutescent; tolerates weak frost; usually cultivated as an annual plant.

*Habit.*—Un-pinched plants develop a flowering main stem, often with additional weaker branches from the base; for commercial purposes, the plants are usually pinched so that 10 or more stems of equal height will be developed.

*Height.*—77 cm (from stem base to tip of 9-week-old plants at the beginning of flowering).

*Width.*—Approximately 16 cm.

*Time to produce a finished flowering plant.*—10-11 weeks for a single-stem plant in a 5-inch pot (spring cultivation); about 13 weeks for a branched plant.

*Outdoor plant performance.*—Use in garden beds or in container planting.

*Time to initiate and develop roots.*—21 days.

*Root description.*—Somewhat fleshy at the base, mainly fibrous.

Leaves:

*Arrangement.*—Opposite and decussate.

*Shape.*—Lanceolate.

*Apex.*—Acuminate.

*Base.*—Sessile.

*Margin.*—Weakly crenate with very short bristles.

*Immature.*—Color: Upper surface: RHS 143C. Lower surface: RHS 138B. Texture: Covered by a very fine pubescence.

*Mature* (*fully expanded*).—Length: 12.5 cm. Width: 3.5 cm. Color: Upper surface: Medium green RHS 137D. Lower surface: Between RHS 138A and RHS 138B. Texture: Smooth, glabrous, and slightly glossy.

*Venation.*—Type: Pinnate with the midrib of the lower surface protruding, and the rest of the venation hardly visible. Color: RHS 145C (greenish white) for lower surface.

Stems:

*Length.*—51 cm 9-week-old plants as measured from the base of the plant, excluding the inflorescence.

*Diameter.*—0.6 cm as measured at the midpoint.

*Internode length.*—5 cm.

*Color.*—RHS 144C.

*Texture.*—Sparse pubescence.

*Anthocyanin.*—RHS 184C (purple brown) may occur in places.

Flower bud:

*Shape.*—Tube-shaped with a closed end.

*Diameter.*—1.1 cm.

*Length.*—2.7 cm.

*Color* (*at tight bud*).—RHS 157A (whitish) with RHS N79B (violet) at the tip.

Inflorescence:

*Inflorescence type.*—Terminal thyrse, narrow, with the peduncles bearing 3 to 7 florets and buds at various stages of development, open flowers are horizontally or somewhat downward directed.

*Blooming habit.*—Intermittent, removing of spent inflorescences enhances development of new flowers.

*Quantity of inflorescence per plant.*—One (for a single stem plant).

*Lastingness of individual blooms on the plant.*—5 to 6 days.

*Fragrance.*—None.

*Inflorescence length.*—25 cm.

*Inflorescence width.*—Up to 11 cm.

*Peduncle.*—Color: RHS 145B (light green). Length: 3 to 5 cm. Diameter: 0.2 to 0.3 cm. Texture: Covered with dense pubescence.

Flower:

*Type.*—Zygomorphic, single funnel-shaped with petals mainly fused, 5-lobed with the free corolla lobes opened outward.

*Floret quantity* (*per raceme*).—30 to 35.

*Shape.*—Funnel-shaped.

*Floret diameter.*—3.0 to 3.5 cm.

*Floret length* (*or depth*).—3.5 to 4 cm.

*Color.*—General: Violet, with a white throat. Corolla lobes: RHS N77A. Corolla (outer surface): RHS 72A to RHS72B and fading towards the base. Corolla (inside surface): RHS N155B to RHS 76D (very pale purple) with fine RHS 71D (purple) lines or veins.

*Petals* (*lobes*).—Quantity: 5. Arrangement: Two upper lobes with two lateral lobes and one lower lobe. Apex: Rounded. Base: Fused and funnel-shaped. Margin: Entire. Texture: Smooth.

*Upper lobes, size.*—Length (from the Corolla opening): 0.9 cm. Width: 1.2 cm.

*Lateral lobes, size.*—Length (from the Corolla opening): 1.1 cm. Width: 1.4 cm.

*Lower lobe.*—Length (from the Corolla opening): 0.9 cm. Width: 1.3 cm.

*Sepals.*—Quantity: 5. Color: RHS 143C. Length: 0.8 cm. Width: 0.6 to 0.7 cm. Shape: Ovate or broadly elliptical. Apex: Acute. Base: Attenuate. Anthocyanin: RHS N77B (violet) which may occur at margins. Texture: Finely pubescent.

*Pedicels.*—Color: RHS 143D. Length: 0.6 cm. Diameter: 0.1 cm. Anthocyanin: RHS 185A (purple-brown) which may occur in stripes. Texture: Finely pubescent.

Reproductive organs:

*Stamens.*—Quantity: 5 total, of which 4 are fertile. Filament: Color: Pure white, lighter than RHS 155D. Length: One pair 2.7 cm, one pair 3.2 cm. Diameter: 0.1 cm. Anther color: RHS N79A (dark violet). Pollen amount: Abundant, typical for the species. Pollen color: RHS 4D (pale yellow).

*Pistils.*—Quantity: 1. Length: 3.2 cm. Stigma color: RHS 155A (white). Style color: RHS 71A (violet) lighter towards the tip.

Fruit and seed set: Plants are fertile; frequently, the ovary is ovate, 0.6 cm in length and 0.4 cm in diameter; when the corolla drops, the ovary develops into a seed capsule (ovate in shape) of about 1.1 cm in length and 0.7 in diameter.

*Seed.*—Color: RHS 200A. Shape: Irregularly round (a few more oblong), wrinkled and pitted. Diameter: 0.15 cm.

Disease and insect resistance: Has not been observed.

COMPARISON WITH PARENTAL AND COMMERCIAL CULTIVARS

'Pheni Vio' differs from the female parent, proprietary *Penstemon* plant '103-3' (unpatented), in that 'Pheni Vio' has violet flowers, while '103-3' has white flowers. Additionally, 'Pheni Vio' has darker green foliage, and is earlier to flower than '103-3'.

'Pheni Vio' differs from the male parent, proprietary *Penstemon* plant '114-1' (unpatented), in that 'Pheni Vio' does not develop any distinct throat markings compared to the violet flowered male parent '114-1'. Additionally, 'Pheni Vio' is earlier to flower and has stronger branching ability than '114-1'.

'Pheni Vio' differs from the commercial cultivar 'Cathedral Hot Rose' (patent status unknown) in that 'Pheni Vio' has larger flowers and a more bluish hue of flower color than 'Cathedral Hot Rose'. Additionally, 'Pheni Vio' flowers earlier than 'Cathedral Hot Rose'.

I claim:

1. A new and distinct cultivar of *Penstemon* plant as shown and described herein.

* * * * *